US007988975B2

(12) United States Patent
Gadelle et al.

(10) Patent No.: US 7,988,975 B2
(45) Date of Patent: Aug. 2, 2011

(54) MODIFIED HIV-1 GROUP M CYCLIC GP41 PEPTIDES AND THEIR USE IN THE DETECTION OF ANTI-HIV-1 ANTIBODIES

(75) Inventors: Stéphane Gadelle, Vauhallan (FR); Francois Rieunier, Bois d'Arcy (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 1112 days.

(21) Appl. No.: 11/659,491

(22) PCT Filed: Jul. 27, 2005

(86) PCT No.: PCT/FR2005/001969
§ 371 (c)(1), (2), (4) Date: Feb. 6, 2007

(87) PCT Pub. No.: WO2006/024752
PCT Pub. Date: Mar. 9, 2006

(65) Prior Publication Data

US 2009/0263785 A1 Oct. 22, 2009

(30) Foreign Application Priority Data

Aug. 6, 2004 (FR) ..................................... 04 08733

(51) Int. Cl.
*A61K 39/21* (2006.01)
*A61K 38/00* (2006.01)
*C12Q 1/70* (2006.01)

(52) U.S. Cl. .......................... 424/188.1; 435/5; 530/333

(58) Field of Classification Search ........................ None
See application file for complete search history.

(56) References Cited

U.S. PATENT DOCUMENTS 4,879,212 A * 11/1989 Wang et al. ....................... 435/5
2004/0072267 A1 4/2004 Rieunier et al.

FOREIGN PATENT DOCUMENTS

EP 0 326 490 A2 8/1989
WO WO 98/45323 A 10/1998

OTHER PUBLICATIONS

Gnann, J. W., et al., 1987, Fine mapping of an immunodominant domain in the transmembrane glycoprotein of human immunodeficiency virus, J. Virol. 61(8):2639-2641.*

* cited by examiner

*Primary Examiner* — Jeffrey Parkin
(74) *Attorney, Agent, or Firm* — Jacobson Holman PLLC

(57) ABSTRACT

The invention involves a synthetic peptide derived from HIV-1 virus gp41 having sequence (SEQ ID NO: 5)

RILAVERYLKDQQLLGIWG$C_{603}$SGKLI$C_{609}$TTAVP$X_{615}$N$aa_1aa_2$ where $X_{615}$ is F or G, a method of preparing the synthetic peptide, a composition and a kit containing the synthetic peptide, and use of the synthetic peptide in immunoassays for the detection of infections caused by HIV-1 viruses.

16 Claims, No Drawings

MODIFIED HIV-1 GROUP M CYCLIC GP41 PEPTIDES AND THEIR USE IN THE DETECTION OF ANTI-HIV-1 ANTIBODIES

This is a 371 of PCT/FR2005/001969 filed 27 Jul. 2005.

The invention relates to synthetic peptides for use in immunological assays for the detection of infections caused by HIV-1 viruses, to a process for their preparation, to compositions and kits comprising such peptides, to the use of such peptides for diagnostic purposes, and to immunological assay processes that employ them for the detection of anti-HIV virus antibodies.

The retrovirus of the HIV-1 type (type 1 human immunodeficiency virus or HIV-1) is known, historically, to be the first agent responsible for AIDS in humans. Today, a distinction is made between HIV-1 type viruses, group M (main group) HIV-1 viruses and group O (outlier group, initially called sub-type O) HIV-1 viruses, which differ, inter alia, genomically and immunologically. Since 1986 (Clavel et al., Science, Vol. 233, pp. 343-346, 18 Jul. 1986), a second type of virus responsible for AIDS in humans, called HIV-2, has been known.

For reasons of economy of expression, group M HIV-1 viruses will be denoted hereinbelow by the expression "HIV-1 M" and group O HIV-1 viruses by the expression "HIV-1 O".

The retrovirus of type HIV-1 was initially discovered in the form of 3 distinct isolates. Those isolates are called LAV, HTLV-III and ARV, which is sometimes also known as ARV-2. Reference may be made to the articles Barré-Sinoussi et al. (Science 20 May 1983, 220, pp. 868-871); Popovic et al. (Science 4 May 1984, 224, pp. 497-500); Gallo et al. (Science 4 May 1984, 224, pp. 500-503) and Levy et al. (Science 24 Aug. 1984, 225, pp. 840-842), which discuss the discovery of those isolates. Those 3 isolates today all form part of the category of the HIV-1 M viruses. The HIV-1 O viruses were described much later, from 1990 onwards, and their isolates had different designations, such as HIV-3 or ANT 70 (European patent application EP 345 375 and De Leys et al., Journal of Virology, March 1990, Vol. 64, No. 3, p. 1207-1216), or, later, MVP5180/91 (Gürtler et al., Journal of Virology, March 1994, Vol. 68, No. 3, p. 1581-1585; European patent application EP 0 591 914), etc. Other group O isolates, such as HIV-1$_{VAU}$, HIV-1$_{DUR}$, MVP2901/94, etc., have since been described.

The sequence of the first isolates of the retrovirus HIV-1 M was elucidated and published at the beginning of 1985: reference may be made to the articles Wain-Hobson et al. (Cell, January 1985, 40, pp. 9-17); Ratner et al. (Nature, 24 Jan. 1985, 313, pp. 277-284); and Sanchez-Pescador et al. (Science 1 Feb. 1985, 227, pp. 484-492). The viruses LAV, HTLV-III and ARV/ARV-2 have since been recognized as being variants of the same AIDS virus, now known by the name HIV-1 (for Human Immunodeficiency Virus) (Ratner et al., Nature, Vol. 313, 21 Feb. 1985, pp. 636-637).

The first in vitro diagnostic assays for infection by HIV-1 M initiated in 1984-1985 were carried out by immunoassay and aimed to detect the presence of anti-HIV-1 M antibodies in human biological samples such as serum or plasma. Those first immunoassays for the detection of anti-HIV-1 M antibodies employed viral lysate as the target antigen for capturing the antibodies to be detected (these are so-called first generation immunoassays). Because they sometimes gave false negative results and/or false positive results owing to the insufficient degree of purity of the antigenic preparation they used, genetic engineering was then turned to in order to produce antigens which were better controlled and more homogeneous and which proved to be more sensitive and more specific. There may be mentioned, for example, the work carried out by several teams on various forms of the antigen of HIV-1 M transmembrane envelope glycoprotein, gp41, and the immunoassays that employed them, which work is documented in the articles Chang et al. (Science, 228, 5 Apr. 1985, pp. 93-96); Crowl et al. (Cell, 41, July 1985, pp. 979-986); Chang et al. (BioTechnology, 3 Oct. 1985, pp. 905-909); Cabradilla et al. (BioTechnology, 4, February, 1986, pp. 128-133), etc. Those immunoassays based on recombinant antigen constituted the second generation immunoassays. Although they brought great progress, those new immunoassays still did not permit detection of all the serums of subjects infected with HIV-1 M.

In the search for still greater sensitivity and specificity, some teams turned to short (generally less than 50 amino acids) synthetic peptides which are easy to produce and control and which can be used as target antigens for the detection of anti-HIV-1 M antibodies. Accordingly, Wang et al. (PNAS, Vol. 83, pp. 6259-6163, August 1986) describe the use of a peptide of the gp41 of an HIV-1 M of sequence RILAVERYLKDQQLLGIWGC$_{603}$S (SEQ ID No 8) as an antibody-capturing antigen.

Likewise, patent application WO86/06414 in the name of Genetic Systems Corporation describes a series of short peptides, some of which are derived from the gp41 of HIV-1 M$_{BRU}$, such as the peptide (X) (39), which corresponds to the very similar sequence RILAVERYLKDQQLLGIWGC$_{603}$SGKLIC$_{609}$ (SEQ ID No 9).

U.S. Pat. No. 4,879,212 (Wang et al.) describes a slightly longer (35 amino acids) peptide of the gp41 of HIV-1 M, of sequence:

(SEQ ID N° 10)
RILAVERYLKDQQLLGIWGC$_{603}$SGKLIC$_{609}$TTAVPWNAS.

The peptides of Wang et al. and those of patent application WO86/06414 confer very great sensitivity and very great specificity on the new peptide-based immunoassays, the so-called third generation immunoassays. A large number of authors have followed the path of short peptides to develop new reagents and, consequently, a large number of commercial anti-HIV antibody detection kits contain them.

The team of John W. Gnann, at the Scripps clinic in La Jolla, California, has even identified in the above peptide (X) (39) an epitope that is very important in diagnostic terms on account of the fact that it is both very immunoreactive and very specific for HIV-1 M: it is the immunodominant epitope —of sequence WGC$_{603}$SGKLIC$_{609}$ (SEQ ID NO: 12)—of the gp41 of HIV-1 M (Gnann et al., Journal of Virology, August 1987, p. 2639-2641; Gnann et al., Science, Vol. 237, 11 Sep. 1987, pp. 1346-1349). Gnann et al. put forward the idea that, in that immunodominant epitope, the formation of a disulfide bridge between the two cysteines C$_{603}$ and C$_{609}$ might play a key role in the antigenic conformation of the epitope by potentially promoting the creation of a cyclic structure.

Shortly afterwards, patent applications WO89/03844 in the name of Ferring AB and EP 0 326 490 A2 in the name of IAF Biochem International described peptides of the gp41 of HIV-1 M carrying "the Gnann et al. epitope" in a form voluntarily cyclized by a disulfide bridge between the two cysteines C$_{603}$ and C$_{609}$, which can be represented in a general, simplified and diagrammatic manner by the following arbitrary formula:

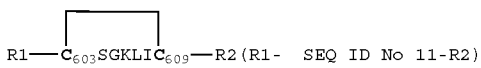
(R1-  SEQ ID No 11-R2)

They confirmed the pioneering intuition of Gnann et al.

Application EP 0 326 490 A2 described, inter alia, the 35 mer peptide of the gp41 of HIV-1 M of U.S. Pat. No. 4,879, 212 (Wang et al.), but in cyclized form and of sequence (I):

(SEQ ID No 7)

RILAVERYLKDQQLLGIWGC₆₀₃SGKLIC₆₀₉TTAVPWNAS (I)

The improvement provided by such peptides so cyclized remains subject to controversy, however, because the latter peptides do not permit the sufficiently early detection of some HIV-1 M seroconversion samples. The performances of the above cyclic peptide of sequence (I) in particular are accordingly still unsatisfactory in terms of sensitivity, given that that peptide does not permit the detection of all seroconversion samples positive for anti-HIV 1 M antibodies and that, furthermore, it poses problems of synthesis yield and solubility.

In short, whichever gp41 peptide is used as the target antigen for the detection of anti-HIV-1 M seroconversions, there still remain some weakly positive samples which are not detected by those third-generation immunoassays. There is therefore a need, in the art, for improved, soluble reagents which can be used for the detection of samples positive for anti-HIV-1 M antibodies. There is a need in particular for reagents having improved sensitivity which allow seroconversions to be detected even earlier. In cases of blood transfusion, it is in fact crucial to detect any sample infected with HIV-1 M as early as possible. A gain of only a week in terms of the detection time is very important in order to avoid, for example, transmitting the virus to a subject receiving a transfusion.

The authors of the present invention began by trying to manufacture a peptide similar to the cyclic peptide of sequence (I), but more easily, that is to say with a better yield. Among the various possible approaches, one consisted simply in reducing the size of the peptide, another in replacing the amino acid residues that might generate a fall in the synthesis yields (problems of solubility, coupling, secondary reactions, etc.). Another possible approach consisted in lengthening the peptide by means of hydrophilic amino acids in order to try and render it more soluble, etc.

The inventors replaced the tryptophan residue at position 615 by different residues in order to obtain a linear peptide (not cyclized between the two cysteine residues) of sequence (II) below:

(SEQ ID N° 6)
RILAVERYLKDQQLLGIWGC₆₀₃SGKLIC₆₀₉TTAVPX₆₁₅Naa₁aa₂

(II)

wherein

X represents an amino acid selected from the group constituted by F and G,
and
wherein the two amino acids aa₁ and aa₂ either are absent or represent
aa₁ : alanine
aa₂ : serine.

As is known to the person skilled in the art, the letters F and G denote the amino acids phenylalanine (F) and glycine (G).

By direct oxidation of the two cysteines on peptides of sequence (II), the inventors then prepared cyclized peptides corresponding to formula (III) below:

(SEQ ID NO: 5)

RILAVERYLKDQQLLGIWGC₆₀₃SGKLIC₆₀₉TTAVPX₆₁₅Naa₁aa₂ wherein

X represents an amino acid selected from the group constituted by F and G,
and
wherein the two amino acids aa₁ and aa₂ either are absent or represent
aa₁ : alanine
aa₂ : serine.

In particular, they have synthesized the following cyclized peptides, designated SEQ ID No 1, No 2, No 3 and No 4, respectively:

SEQ ID No 1:

RILAVERYLKDQQLLGIWGCSGKLICTTAVPF₆₁₅NA₆₁₇S₆₁₈

SEQ ID No 2:

RILAVERYLKDQQLLGIWGCSGKLICTTAVPF₆₁₅N

SEQ ID No 3:

RILAVERYLKDQQLLGIWGCSGKLICTTAVPG₆₁₅N

SEQ ID No 4:

RILAVERYLKDQQLLGIWGCSGKLICTTAVPG₆₁₅N A₆₁₇S₆₁₈

In a surprising and totally unexpected manner, given on the one hand that the long sequence for some peptides was initially shortened by 35 amino acids, with the risk of losing a functional epitope, and on the other hand that partially artificial sequences were generated which are not found in natural viral strains, the inventors have found that, by so modifying the cyclic peptide of formula (I) of the prior art, which did not detect all seroconversion samples positive for anti-HIV-1 M antibodies, novel peptides, the peptides of sequence (III), which were capable of detecting all those samples, were obtained.

The present invention accordingly relates to a cyclic peptide of HIV-1 virus gp41 of sequence (III):

(SEQ ID NO: 5)

RILAVERYLKDQQLLGIWGC₆₀₃SGKLIC₆₀₉TTAVPX₆₁₅Naa₁aa₂ wherein

X represents an amino acid selected from the group constituted by F and G, and
wherein the two amino acids $aa_1$ and $aa_2$ either are absent or represent
$aa_1$ : alanine
$aa_2$ : serine.

The present invention relates also to a composition, in particular an antigenic composition, comprising a peptide of sequence (III).

The present invention relates further to a peptide of HIV-1 virus gp41 of sequence (III) selected from the group constituted by the following peptides:

SEQ ID No 1:
RILAVERYLKDQQLLGIWGCSGKLICTTAVP$F_{615}$N$A_{617}S_{618}$ SEQ ID No 2:
RILAVERYLKDQQLLGIWGCSGKLICTTAVP$F_{615}$N SEQ ID No 3:
RILAVERYLKDQQLLGIWGCSGKLICTTAVP$G_{615}$N SEQ ID No 4:
RILAVERYLKDQQLLGIWGCSGKLICTTAVP$G_{615}$N $A_{617}S_{618}$ The present invention relates also to a composition, in particular an antigenic composition, comprising a peptide of sequence (III) selected from the group constituted by the peptides SEQ ID No 1 to 4 shown above.

Within the scope of the present invention, "composition" is understood as meaning any liquid or solid association of a plurality of molecular components. Some compositions, or mixtures, are constituted by liquid or solid aqueous solutions comprising one or more chemical components that are of interest. Such an aqueous solution can be constituted by a buffer, having a pH that is generally close to neutral (preferably from pH 5 to pH 9), preferably in association with one or more protides (i.e. proteins, polypeptides, oligopeptides and/or amino acids) used for the desired object. Among the buffers known to the person skilled in the art, mention may be made, without implying any limitation, of phosphate, carbonate, Tris, borate, etc. buffers. Among the proteins which can be used in the buffers, there may be mentioned, inter alia, bovine serum albumin (BSA), etc. A preservative, such as sodium azide, for example, is often added to such compositions, as well as, optionally, a detergent.

Within the scope of the present invention, "antigenic composition" is understood as meaning any composition mentioned above comprising at least one peptide according to the invention (of sequence (III)) in a form such that it substantially retains its initial antigenic reactivity, that is to say its capacity to be recognized by anti-HIV antibodies. Such antigenic compositions can also incorporate an HIV-2 antigen and/or an HIV-1 O antigen, of which the immunoreactivity is maintained.

Such antigenic compositions can be used for the in vitro diagnostics, in a sample of human biological fluid, of an HIV infection and, in particular but not exclusively, for the detection of anti-HIV antibodies, according to any form of immunoassay protocol known per se to the person skilled in the art (see, inter alia, the section "More detailed description of the invention" hereinbelow, in paragraph 4).

Such antigenic compositions can be incorporated in liquid or dry form into kits for the in vitro diagnostics of an HIV infection, in particular into kits for the detection of anti-HIV antibodies. Such antigenic compositions can be immobilized on a solid phase or can be incorporated into a detection antigen, such as a labelled antigen, especially an antigen labelled with an enzyme, etc., according to methods known per se to the person skilled in the art.

The present invention relates further to a process for the preparation of a peptide of sequence (III), especially of a peptide selected from the group constituted by the peptides SEQ ID No 1, SEQ ID No 2, SEQ ID No 3 and SEQ ID No 4.

The present invention relates further to a process for the preparation of a composition comprising a peptide of sequence (III), especially a peptide selected from the group constituted by the peptides SEQ ID No 1, SEQ ID No 2, SEQ ID No 3 and SEQ ID No 4.

The present invention relates further to a method for the detection of anti-HIV antibodies in a biological sample, comprising
a) bringing the biological sample into contact either with a peptide of HIV-1 virus gp41 of sequence (III), especially a peptide selected from the group constituted by the peptides SEQ ID No 1, SEQ ID No 2, SEQ ID No 3 and SEQ ID No 4, and/or with a composition comprising such a peptide; or with a combination of peptides of sequence (III);
b) incubating the mixture under conditions that permit the formation of antigen-antibody complexes; and
c) revealing and detecting the antigen-antibody complexes that have formed by a detection means, optionally constituted by an HIV-1 antigen, which can, where appropriate, comprise a labelled peptide of sequence (III) according to the invention capable of binding to a captured anti-HIV-1 antibody.

The present invention relates also to the preceding anti-HIV antibody detection method in which step a) comprises bringing the biological sample into contact with a mixture constituted by at least one gp41 peptide of sequence (III) according to the invention and an HIV-2 antigen and/or an HIV-1 O antigen.

The present invention relates also to a kit for the detection of anti-HIV antibodies in a biological sample, comprising a peptide of HIV-1 virus gp41 of sequence (III), especially a peptide selected from the group constituted by the peptides SEQ ID No 1, SEQ ID No 2, SEQ ID No 3 and SEQ ID No 4, or a composition comprising such a peptide, optionally in association with an HIV-2 antigen and/or an HIV-1 O antigen.

The present invention relates further to the use of at least one peptide of HIV-1 virus gp41 of sequence (III), especially a peptide selected from the group constituted by the peptides SEQ ID No 1, SEQ ID No 2, SEQ ID No 3 and SEQ ID No 4, optionally in association with an HIV-2 antigen and/or an HIV-1 O antigen, for detecting anti-HIV virus antibodies.

MORE DETAILED DESCRIPTION OF THE INVENTION

1. Biological Samples:
Within the scope of the present invention, the expression "biological sample" is understood as meaning a sample of any human body fluid such as blood, serum, plasma, saliva, tears, sperm, cephalorachidian fluid and any other body fluid that may contain anti-HIV antibodies.

2. Preparation of the Peptides According to the Invention:
The peptides of sequence (III) according to the invention are preferably, because it is more practical, but not exclusively, produced by conventional techniques known to the person skilled in the art. There may be mentioned as an example the Merrifield type synthesis (Merrifield, *J. Am. Chem. Soc.* 85, pp. 2149-2154, 1963). It is also possible to use the synthesis of the "Fmoc" (9-fluorenylmethyloxycarbonyl) type, which is advantageous for reasons of purity, antigenic specificity, absence of undesirable secondary products and for its ease of use.

The peptide synthesis can be automated by means of synthesizers, for example of the "Pioneer" synthesizer type from Perspective, of the "433A" synthesizer type from ABI (Applied Biosystems Inc.) or of the "Symphony" type from Rainin.

The peptides can likewise be obtained by synthesis in homogeneous phase according to techniques known per se to the person skilled in the art.

The cyclization of linear peptides in order to obtain cyclized peptides of formula (III) according to the invention can be carried out by various methods known per se to the person skilled in the art, in particular according to one of the methods described in patent applications WO89/03844 (chemical oxidation step with iodine in methanolic solution) and EP 0 326 490 A2 (potassium ferricyanide method).

By methods known per se to the person skilled in the art, the peptides according to the invention can optionally be incorporated into buffers, in the presence of proteins, polypeptides, oligopeptides or amino acids and other chemical compounds used to constitute antigenic compositions according to the invention.

3. Other HIV Antigens which can be Used in the Method for the Detection of Anti-HIV Antibodies and in the Anti-HIV Antibody Detection Kit According to the Invention:

As HIV-2 antigen there can be used a variety of antigens, preferably the gp140 or the transmembrane glycoprotein gp36 of HIV-2, more preferably a peptide containing at least the immunodominant epitope (of gp36) of Gnann et al., that is to say comprising at least the amino acids WGCAFRQVC (SEQ ID NO: 13) (see, for example, the article Gnann et al., Science, Vol. 237, 11 Sep. 1987, pp. 1346-1349; the article Guyader et al., Nature 16 Apr. 1987, 326, pp. 662 669, which describes the complete sequence of HIV-2$_{ROD}$, or the env sequence given in patent EP 0 239 425), still more preferably a peptide comprising at least the amino acids WGCAFRQVC (SEQ ID NO: 13) in a form cyclized by a disulfide bridge between the two cysteines.

As HIV-1 O antigen there can be used a variety of antigens, preferably the gp160 or gp41 of HIV-1 O. More preferably, it is possible to use a peptide containing the immunodominant epitope (gp41) of Gnann et al. comprising, for example, at least the amino acids WGCKGKLIC (SEQ ID NO: 14) (of MVP5180/91, described in the env sequence of patent application EP 0 591 914, or sequence obtainable from the GenBank databank under accession number L20571, see Gürtler et al., Journal of Virology, March 1994, Vol. 68, No. 3, p. 1581-1585). Yet more preferably, it is possible to use a peptide comprising at least the amino acids WGCKGKLIC (SEQ ID NO: 14) in a form cyclized by a disulfide bridge between the two cysteines.

Alternatively, there can be used as HIV-1 O antigen, for example, the amino acids WGCKGKLVC (SEQ ID NO: 15) (of HIV-3/ANT70, sequence obtainable from the GenBank databank under accession number L20587, see Gürtler et al., Journal of Virology, March 1994, Vol. 68, No. 3, p. 1581-1585). Yet more preferably, it is possible to use a peptide comprising at least the amino acids WGCKGKLVC (SEQ ID NO: 15) in a form cyclized by a disulfide bridge between the two cysteines.

4. Methods of Carrying Out the Method for the Detection of Anti-HIV Antibodies According to the Invention:

With regard to possible methods of carrying out the method for the detection of anti-HIV antibodies according to the invention, reference can advantageously be made, for example, to the review "A Decade of Development In Immunoassay Methodology" by James P. Gosling, Clinical Chemistry, 36/8, pp. 1408-1427, (1990), which mentions a large number of technologies and variants that are available and known in immunoassays.

The method for the detection of anti-HIV antibodies in a biological sample can be carried out by any immunoassay, in the broad sense, that is to say an immunological assay involving the formation of an immune complex between at least one peptide according to the invention and at least one anti-HIV antibody. The methods of immunological assay, or immunoassays, are well known to the person skilled in the art and can be of the type EIA (Enzyme Immuno Assay), ELISA (Enzyme Linked Immuno Sorbent Assay), RIA (Radio Immuno Assay), FIA (Fluoro Immuno Assay), etc., depending on the marker and the labelled reagent that are chosen.

The term "labelled" refers both to direct labelling (by means of enzymes, radioisotopes, fluorochromes, luminescent compounds, etc.) and to indirect labelling (for example by means of antibodies that are themselves labelled directly or by means of reagents of a labelled "affinity pair", such as, but not exclusively, the pair labelled avidine-biotin, etc.). The detection means of the method for the detection of anti-HIV antibodies according to the invention can, for example, but not exclusively, be constituted by a labelled HIV antigen, a labelled human anti-immunoglobulin antibody or any other molecule having affinity for an immunoglobulin, such as protein A or protein G, in labelled form, etc. It is possible to use as marker an enzyme, a radioisotope, a fluorochrome, a luminescent compound, etc., which is coupled in a manner known per se to said peptide according to the invention or to said anti-immunoglobulin antibody or to any other molecule chosen as detection means (for example protein A or protein G).

Within the scope of the present invention, peptides can be labelled by means of Raifort peroxidase according to a protocol known per se, such as the technique of Nakane and Kawaoki (J. Histochem. Cytochem. 22, p. 1984 (1974)), or any other coupling technique known to the person skilled in the art. Other enzymes, such as alkaline phosphatase, etc., can be used.

The method for the detection of anti-HIV antibodies according to the invention can be carried out in solid phase (heterogeneous assay) or in liquid phase (homogeneous assay).

The detection of anti-HIV antibodies according to the invention can cover various protocols known to the person skilled in the art: protocols of the competitive type, of the indirect type or alternatively of the conventional antigen-antibody-antigen sandwich type, also called the "double-antigen sandwich" method (Maiolini et al., Journal of Immunological Methods, 20 (1978) 25-34), in one stage or in two stages.

According to a preferred embodiment of the invention in heterogeneous phase, in a protocol of the indirect type or in a "double-antigen sandwich" method, an HIV-1 M envelope antigen corresponding to gp160, to gp41 or to a peptide according to the invention, used in association or not with an HIV-2 antigen and/or an HIV-1 O antigen, as antibody-capturing antigen, is immobilized on a solid phase. It is possible to use, as non-limiting examples of solid phases, microplates, in particular polystyrene microplates, such as those marketed by Nunc, Denmark. It is also possible to use particles or solid beads, paramagnetic beads, such as those supplied by Dynal or Merck-Eurolab (France) (under trade mark Estapor™) or polystyrene or polypropylene test tubes, nitrocellulose strips, etc.

According to a preferred embodiment, within the scope of the "double-antigen sandwich" method (Maiolini et al., 1978), a peptide according to the invention is used in labelled form as detection means, i.e. as the antigen for revealing the complexes formed and immobilized on the solid phase.

According to another preferred embodiment, within the scope of the protocol of the indirect type, a human anti-immunoglobulin antibody, or an immunoreactive fragment (Fab, Fab', etc.) of that antibody, can be used in labelled form as the detection means, i.e. as the antibody for revealing the complexes formed and immobilized on the solid phase.

5. Anti-HIV Antibody Detection Kits

The kits and reagents used for the detection of anti-HIV antibodies in a biological sample, according to the method of the invention, can be supplied for implementing the invention in a simple manner that is applicable to a number of biological samples.

The invention therefore relates to a kit for the detection of anti-HIV antibodies in a biological sample, comprising:
  at least one capture and/or detection antigen, which is a peptide that can be constituted by a peptide of sequence (III) according to the invention or by an antigenic composition containing such a peptide;
  at least one means for detecting the antigen-antibody complexes that form.

Advantageously, the kit can comprise a plurality of capture and/or detection antigens.

As has been described above, the capture antigen can advantageously be present in a form immobilized on a solid phase, such as a microplate.

A preferred kit for the detection of anti-HIV antibodies in a biological sample comprises:
a) a capture antigen, which is a peptide of sequence (III) according to the invention or an antigenic composition containing such a peptide, said capture antigen being immobilized on a microplate;
b) a detection antigen, labelled by an enzyme.

Another preferred kit for the detection of anti-HIV antibodies in a biological sample comprises
a) a capture antigen, said capture antigen being immobilized on a microplate;
b) a detection antigen, labelled by an enzyme, that is a peptide of sequence (III) according to the invention or a composition containing such a peptide.

Another preferred kit for the detection of anti-HIV antibodies in a biological sample comprises
a) a capture antigen that is a peptide of sequence (III) according to the invention, said capture antigen being immobilized on a microplate;
b) a labelled anti-immunoglobulin antibody, especially an anti-immunoglobulin antibody labelled by an enzyme.

The Examples which follow illustrate the invention without limiting the scope thereof.

EXAMPLE 1

Synthesis of Peptides

The following syntheses were carried out on a Pioneer synthesizer using "Fmoc" (9-fluorenylmethyloxycarbonyl) chemistry: in each step, the reagents (that is to say the protected amino acid and the coupling activators (TBTU (2-(1H-benzotriazol-1-yl)-1,1,3,3-tetramethyluronium tetrafluoroborate)/HOBt (N-hydroxybenzotriazole)) are added in excess (in a ratio "moles of reagents/moles of substitutable groups on the resin"=5). At the end of the synthesis, the peptide is separated from the resin by a solution based on trifluoroacetic acid (reagent K). The peptide is then precipitated in a cooled ether solution and then purified by HPLC.

A chemical oxidation step is carried out on each synthesized linear peptide, allowing the peptide to be cyclized in the region of the 2 cysteines.

In that manner, the inventors have carried out the synthesis of the following cyclized peptides:

(SEQ ID No 10)

RILAVERYLKDQQLLGIWG$\overline{\text{C}}$SGKLI$\overline{\text{C}}$TTAVPW$_{615}$NA$_{617}$S$_{618}$ This peptide of sequence SEQ ID No 10 was synthesized and used in the experiments described hereinbelow because, according to the inventors, it represents the most similar peptide of the prior art. It is therefore used in the comparisons described hereinbelow.

SEQ ID No 1:

RILAVERYLKDQQLLGIWG$\overline{\text{C}}$SGKLI$\overline{\text{C}}$TTAVPF$_{615}$NA$_{617}$S$_{618}$ SEQ ID No 2:

RILAVERYLKDQQLLGIWG$\overline{\text{C}}$SGKLI$\overline{\text{C}}$TTAVPF$_{615}$N

SEQ ID No 3:

RILAVERYLKDQQLLGIWG$\overline{\text{C}}$SGKLI$\overline{\text{C}}$TTAVPG$_{615}$N

SEQ ID No 4:

RILAVERYLKDQQLLGIWG$\overline{\text{C}}$SGKLI$\overline{\text{C}}$TTAVPG$_{615}$N A$_{617}$S$_{618}$ Each of those peptides was conjugated to Raifort peroxidase (labelled conjugate) according to the well known method of Nakane and Kawaoi (J. Histochem. Cytochem. 22, p. 1984 (1974)).

EXAMPLE 2

Serum Samples Used

The serums used for the detection of anti-HIV antibodies are:
  samples of seroconversion panels supplied by Boston Biomedica Inc. (7 panels; 17 samples), Nabi (5 panels; 14 samples) and Impath Bioclinical Partners (4 BCP panels; 10 samples);
  4 serum samples positive for anti-HIV-1 antibodies (C4, C5, C9 and C10) of an internal panel from Bio-Rad, Marnes la Coquette, 92430, France;
  13 serums from normal donors and from negative subjects were additionally tested in order to determined the cut-off of the assays.

EXAMPLE 3

Immunoenzyme Assay Using the Peroxidase-HIV 1 Peptide Conjugates

The detection of antibodies directed against the HIV viruses is based, in the example below, on the principle of the immunoenzyme technique of the "double-antigen sandwich" type. The test is based on the use, on the one hand, of a microplate (solid phase) sensitized with purified antigens, including the HIV-1 M virus envelope glycoprotein (gp160), and, on the other hand, of a conjugate constituted by a peptide according to the invention labelled with peroxidase, which take an anti-HIV antibody to be detected into a sandwich.

The assay protocol used is as follows: 100 µl of each serum sample tested, diluted to ¾, are distributed in a well of the sensitized microplate and the mixture is homogenized. After incubation of the mixture under adhesive film for 60 minutes at 37° C., followed by washing of the microplate by means of a Tris NaCl buffer, 100 µl of labelled conjugate (peroxidase-labelled HIV-1 peptide according to the invention) are added to each well. The mixture is incubated under adhesive film for 30 minutes at 18-30° C.

After removal, by washing with the above-mentioned Tris NaCl buffer, of the conjugate fraction that has remained free, the presence of the immobilized enzyme on the complexes is revealed. To that end, 80 µl of a revelation solution (containing $H_2O_2$ substrate in a solution of citric acid and sodium acetate, and a chromogenic compound, tetramethylbenzidine or TMB) are added to each well. After incubation of the mixture again in darkness for 30 minutes at 18-30° C., the revelation is stopped by addition of 100 µl of 1N sulfuric acid. The optical density is read on a spectrophotometer at 450/620 nm.

The presence or absence of anti-HIV antibodies is determined by comparing, for each sample tested, the recorded optical density ("OD") with that of the calculated cut-off (cut-off=average of the OD of negative samples+0.100 OD unit).

A sample is considered to be positive (carrier of anti-HIV antibodies) if the OD obtained is greater than that of the cut-off, and negative if its OD is lower than that of the cut-off.

Table I shows the comparative results obtained by means of the 5 conjugates produced under the same conditions (coupling of each peptide synthesized above with peroxidase). The various conjugates prepared are described hereinbelow:

conjugate A: peptide of sequence SEQ ID No 10 coupled with peroxidase conjugate B: peptide of SEQ ID No 1 coupled with peroxidase conjugate C: peptide of SEQ ID No 2 coupled with peroxidase conjugate D: peptide of SEQ ID No 3 coupled with peroxidase conjugate E: peptide of SEQ ID No 4 coupled with peroxidase In Table I below, the results given are OD values read after immunoenzyme assays carried out according to the protocol described above and using the described conjugates A, B, C, D and E.

TABLE I

Results expressed in optical density units

| | Conjugate | | | | |
|---|---|---|---|---|---|
| | A | B | C | D | E |
| Positive serum Internal panel | | | | | |
| C4 | 0.107 | 0.204 | 0.153 | 0.230 | 0.220 |
| C5 | 0.099 | 0.186 | 0.121 | 0.181 | 0.189 |
| C9 | 0.129 | 0.196 | 0.206 | 0.179 | 0.174 |
| C10 | 0.309 | 0.388 | 0.341 | 0.376 | 0.353 |
| Positive serum BCP panel | | | | | |
| 9017-3 | 0.025 | 0.054 | 0.044 | 0.053 | 0.044 |
| 9017-4 | 0.070 | 0.134 | 0.118 | 0.136 | 0.098 |
| 9017-5 | 0.144 | 0.254 | 0.219 | 0.229 | 0.191 |
| 9021-15 | 0.023 | 0.021 | 0.021 | 0.012 | 0.044 |
| 9021-16 | 0.139 | 0.231 | 0.187 | 0.107 | 0.098 |
| 9021-17 | 2.214 | 2.868 | 2.500 | 1.925 | 0.191 |
| 9023-21 | 0.009 | 0.013 | 0.011 | 0.010 | 0.017 |
| 9023-22 | 0.257 | 0.404 | 0.309 | 0.402 | 0.380 |
| 9032-8 | 0.010 | 0.035 | 0.017 | 0.026 | 0.033 |
| 9032-9 | 0.244 | 0.330 | 0.252 | 0.299 | 0.314 |
| Positive serum BBI panel | | | | | |
| W9 | 0.016 | 0.023 | 0.019 | 0.017 | 0.015 |
| W10 | 2.386 | 3.093 | 2.892 | 2.748 | 2.794 |
| AQ3 | 0.017 | 0.014 | 0.015 | 0.008 | 0.012 |
| AQ4 | 0.282 | 0.322 | 0.274 | 0.295 | 0.290 |
| AT3 | 0.014 | 0.017 | 0.015 | 0.016 | 0.016 |
| AT4 | 0.082 | 0.115 | 0.092 | 0.115 | 0.105 |
| AT5 | 3.749 | 3.746 | 3.816 | 3.875 | 3.719 |
| BC3 | 0.096 | 0.078 | 0.091 | 0.090 | 0.073 |
| BC4 | 2.349 | 2.413 | 2.308 | 2.382 | 2.346 |
| BF4 | 0.007 | 0.009 | 0.009 | 0.010 | 0.007 |
| BF5 | 0.148 | 0.196 | 0.170 | 0.200 | 0.190 |
| BG5 | 0.008 | 0.011 | 0.009 | 0.009 | 0.010 |
| BG6 | 0.200 | 0.289 | 0.234 | 0.266 | 0.278 |
| BG7 | 3.455 | 3.720 | 3.540 | 3.730 | 3.674 |
| BI1 | 0.008 | 0.010 | 0.010 | 0.010 | 0.009 |
| BI2 | 0.068 | 0.122 | 0.088 | 0.121 | 0.105 |
| BI3 | 1.642 | 1.494 | 1.607 | 1.598 | 1.563 |
| Positive serum NABI panel | | | | | |
| 241-B | 0.063 | 0.080 | 0.067 | 0.076 | 0.077 |
| 241-C | 0.070 | 0.114 | 0.099 | 0.114 | 0.110 |
| 241-D | 3.838 | 3.867 | 3.795 | 3.770 | 3.745 |
| 271-C | 0.022 | 0.047 | 0.037 | 0.030 | 0.023 |
| 271-D | 0.637 | 1.304 | 0.975 | 0.463 | 0.499 |
| 401-C | 0.008 | 0.012 | 0.010 | 0.010 | 0.009 |
| 401-D | 0.091 | 0.275 | 0.164 | 0.231 | 0.247 |
| 401-E | 1.395 | 2.226 | 1.784 | 2.263 | 2.333 |
| 407-D | 0.007 | 0.011 | 0.010 | 0.010 | 0.011 |
| 407-E | 0.105 | 0.121 | 0.110 | 0.090 | 0.087 |
| 407-F | 3.923 | 4.000 | 3.830 | 4.000 | 4.000 |
| 409-B | 0.007 | 0.010 | 0.009 | 0.007 | 0.007 |
| 409-C | 0.091 | 0.146 | 0.114 | 0.141 | 0.144 |
| 409-D | 1.334 | 1.811 | 1.528 | 1.889 | 1.868 |
| Negative serums N = 13 | | | | | |
| Average | 0.008 | 0.009 | 0.009 | 0.010 | 0.009 |
| Cut-off | 0.108 | 0.109 | 0.109 | 0.110 | 0.109 |

Conjugates B, C, D and E obtained with peptides according to the invention give, for the positive samples tested, and with an almost identical cut-off, an OD value that is significantly greater than that obtained with conjugate A of the 35 mer peptide of the prior art (peptide of sequence (SEQ ID No 10)).

In Table II below, the same results are expressed as the sample OD/cut-off (OD/CO) ratio.

TABLE II

Results expressed as optical density/cut-off ratio

| | Conjugate | | | | |
|---|---|---|---|---|---|
| | A | B | C | D | E |
| Positive serum Internal panel | | | | | |
| C4 | 0.99 | 1.87 | 1.39 | 2.09 | 2.02 |
| C5 | 0.92 | 1.71 | 1.10 | 1.65 | 1.73 |
| C9 | 1.19 | 1.80 | 1.87 | 1.63 | 1.60 |
| C10 | 2.86 | 3.56 | 3.10 | 3.42 | 3.24 |
| Positive serum BCP panel | | | | | |
| 9017-3 | 0.23 | 0.50 | 0.40 | 0.48 | 0.40 |
| 9017-4 | 0.65 | 1.23 | 1.07 | 1.24 | 0.90 |
| 9017-5 | 1.33 | 2.33 | 1.99 | 2.08 | 1.75 |
| 9021-15 | 0.21 | 0.19 | 0.19 | 0.11 | 0.19 |
| 9021-16 | 1.29 | 2.12 | 1.70 | 0.97 | 1.06 |
| 9021-17 | 20.50 | 26.31 | 22.73 | 1.50 | 17.92 |
| 9023-21 | 0.08 | 0.12 | 0.10 | 0.09 | 0.16 |
| 9023-22 | 2.38 | 3.71 | 2.81 | 3.65 | 3.49 |
| 9032-8 | 0.09 | 0.32 | 0.16 | 0.24 | 0.30 |
| 9032-9 | 2.26 | 3.03 | 2.29 | 2.72 | 2.88 |
| Positive serum BBI panel | | | | | |
| W9 | 0.15 | 0.21 | 0.18 | 0.15 | 0.14 |
| W10 | 26.26 | 28.38 | 26.29 | 24.98 | 25.63 |
| AQ3 | 0.16 | 0.13 | 0.14 | 0.07 | 0.11 |
| AQ4 | 2.61 | 2.95 | 2.49 | 2.68 | 2.66 |
| AT3 | 0.13 | 0.16 | 0.13 | 0.15 | 0.15 |
| AT4 | 0.76 | 1.06 | 0.84 | 1.05 | 0.96 |
| AT5 | 34.71 | 34.37 | 34.69 | 35.23 | 34.12 |
| BC3 | 0.89 | 0.72 | 0.82 | 0.82 | 0.67 |
| BC4 | 21.75 | 22.14 | 20.98 | 21.65 | 21.52 |
| BF4 | 0.06 | 0.08 | 0.08 | 0.09 | 0.06 |
| BF5 | 1.37 | 1.80 | 1.54 | 1.82 | 1.74 |
| BG5 | 0.07 | 0.10 | 0.08 | 0.08 | 0.09 |
| BG6 | 1.85 | 2.65 | 2.13 | 2.42 | 2.55 |
| BG7 | 31.99 | 34.13 | 32.18 | 33.91 | 33.71 |
| BI1 | 0.07 | 0.09 | 0.09 | 0.09 | 0.08 |
| BI2 | 0.63 | 1.12 | 0.80 | 1.10 | 0.96 |
| BI3 | 15.20 | 13.71 | 14.61 | 14.53 | 14.34 |
| Positive serum NABI panel | | | | | |
| 241-B | 0.58 | 0.73 | 0.60 | 0.69 | 0.71 |
| 241-C | 0.65 | 1.05 | 0.90 | 1.04 | 1.01 |
| 241-D | 35.54 | 35.48 | 34.50 | 34.27 | 34.36 |
| 271-C | 0.20 | 0.43 | 0.34 | 0.27 | 0.21 |
| 271-D | 5.90 | 11.96 | 8.86 | 4.21 | 4.58 |
| 401-C | 0.07 | 0.11 | 0.09 | 0.09 | 0.08 |
| 401-D | 0.84 | 2.52 | 1.49 | 2.10 | 2.27 |
| 401-E | 12.92 | 20.42 | 16.21 | 20.57 | 21.40 |
| 407-D | 0.06 | 0.10 | 0.09 | 0.09 | 0.10 |
| 407-E | 0.97 | 1.11 | 1.00 | 0.82 | 0.80 |
| 407-F | 36.32 | 36.70 | 34.82 | 36.36 | 36.70 |
| 409-B | 0.06 | 0.09 | 0.08 | 0.06 | 0.06 |
| 409-C | 0.84 | 1.34 | 1.03 | 1.28 | 1.32 |
| 409-D | 12.35 | 16.61 | 13.89 | 17.17 | 17.14 |

With an almost identical cut-off, conjugates B, C, D and E obtained with peptides according to the invention give, for the samples tested, OD/CO ratios that are significantly greater than those obtained with conjugate A of the 35 mer peptide of the prior art (peptide of sequence SEQ ID No 10). Likewise, some negative samples with conjugate A of the peptide of the prior art are found to be positive with the peptides according to the invention.

The table of results expressed as OD/CO ratio (Table III) shows the distribution of the samples as a function of the OD/CO ratios obtained:

TABLE III

| Positive serums | Conjugate | | | | |
|---|---|---|---|---|---|
| N = 45 | A | B | C | D | E |
| OD/CO ratio <1 | 25 | 16 | 19 | 19 | 20 |
| OD/CO ratio >1 | 20 | 29 | 26 | 26 | 25 |

Table III clearly shows that the positive serums tested are detected better with the peptides according to the invention than with the peptide of the prior art of sequence SEQ ID No 10 (conjugate A), because the number of samples giving a OD/CO ratio greater than 1 is significantly higher.

As is shown by Tables I, II and III overall, the peptides according to the invention (conjugates B, C, D and E of sequence (III)) permit the significantly earlier detection of seroconversions than does the peptide of the prior art of sequence SEQ ID No 10 (conjugate A).

In Table IV below, the immunoreactivity of conjugates B, C, D and E is given as a percentage of the immunoreactivity of conjugate A, which represents the reference.

TABLE IV

Results expressed as percentage immunoreactivity relative to conjugate A

| | Conjugate | | | |
|---|---|---|---|---|
| | B | C | D | E |
| Positive serum Internal panel | | | | |
| C4 | 191% | 133% | 215% | 206% |
| C5 | 188% | 113% | 183% | 191% |
| C9 | 152% | 168% | 139% | 135% |
| C10 | 126% | 109% | 122% | 114% |
| Positive serum BCP panel | | | | |
| 9017-3 | 216% | 180% | 212% | 176% |
| 9017-4 | 191% | 161% | 194% | 140% |
| 9017-5 | 176% | 150% | 159% | 133% |
| 9021-15 | 91% | 95% | 52% | 91% |
| 9021-16 | 166% | 129% | 77% | 83% |
| 9021-17 | 130% | 109% | 87% | 88% |
| 9023-21 | 144% | 108% | 111% | 189% |
| 9023-22 | 157% | 111% | 156% | 148% |
| 9032-8 | 350% | 158% | 260% | 330% |
| 9032-9 | 135% | 102% | 123% | 129% |
| Positive serum BBI panel | | | | |
| W9 | 144% | 113% | 106% | 94% |
| W10 | 109% | 101% | 97% | 99% |
| AQ3 | 82% | 96% | 47% | 71% |
| AQ4 | 114% | 94% | 105% | 103% |
| AT3 | 121% | 107% | 114% | 114% |
| AT4 | 140% | 109% | 140% | 128% |
| AT5 | 100% | 101% | 103% | 99% |
| BC3 | 81% | 98% | 94% | 76% |
| BC4 | 103% | 98% | 101% | 100% |
| BF4 | 129% | 119% | 143% | 100% |
| BF5 | 132% | 111% | 135% | 128% |
| BG5 | 138% | 112% | 113% | 125% |
| BG6 | 145% | 113% | 133% | 139% |
| BG7 | 108% | 101% | 108% | 106% |
| BI1 | 125% | 133% | 125% | 113% |
| BI2 | 179% | 120% | 178% | 154% |
| BI3 | 91% | 98% | 97% | 95% |
| Positive serum NABI panel | | | | |
| 241-B | 127% | 99% | 121% | 122% |
| 241-C | 163% | 129% | 163% | 157% |

TABLE IV-continued

Results expressed as percentage immunoreactivity relative to conjugate A

| | Conjugate | | | |
|---|---|---|---|---|
| | B | C | D | E |
| 241-D | 101% | 98% | 98% | 98% |
| 271-C | 214% | 140% | 136% | 105% |
| 271-D | 205% | 139% | 73% | 98% |
| 401-C | 150% | 117% | 125% | 113% |
| 401-D | 302% | 166% | 254% | 271% |
| 401-E | 160% | 121% | 162% | 167% |
| 407-D | 157% | 133% | 143% | 157% |
| 407-E | 115% | 105% | 86% | 83% |
| 407-F | 102% | 97% | 102% | 102% |
| 409-B | 143% | 120% | 100% | 100% |
| 409-C | 160% | 118% | 155% | 158% |
| 409-D | 136% | 110% | 142% | 140% |

Table IV clearly shows that the peptides according to the invention (conjugates B, C, D and E of sequence (III)) have an immunoreactivity that is generally significantly greater than that of the peptide of the prior art of sequence SEQ ID No 10 and therefore have a generally higher detection sensitivity.

In summary, all the results above show that the serums positive for anti-HIV-1 antibodies that were tested are detected by the peptides according to the invention (conjugates B, C, D and E of sequence (III)) in a significantly superior manner to the detection obtained by a peptide of the prior art (conjugate A of sequence SEQ ID No 10), the most similar peptide. Moreover, the peptides according to the invention (conjugates B, C, D and E of sequence (III)) permit seroconversions to be detected even earlier.

The invention therefore achieves the stated object well, by means of the peptides according to the invention.

The inventions claimed is:

1. An isolated cyclic peptide of human immunodeficiency virus type 1 (HIV-1) gp41 consisting of (SEQ ID NO: 5)
$$\text{RILAVERYLKDQQLLGIWG}\overset{\frown}{\text{C}_{603}\text{SGKLIC}_{609}}\text{TTAVPX}_{615}\text{Naa}_1\text{aa}_2$$

wherein X is an amino acid selected from the group consisting of F and G, and wherein (i) $aa_1$ and $aa_2$ are absent or (ii) $aa_1$ is alanine and $aa_2$ is serine.

2. An antigenic composition comprising a peptide according to claim 1 in combination with a carrier or diluent.

3. The peptide according to claim 1, wherein the peptide consists of (SEQ ID NO: 1)
$$\text{RILAVERYLKDQQLLGIWG}\overset{\frown}{\text{C}_{603}\text{SGKLIC}_{609}}\text{TTAVPF}_{615}\textbf{NA}_{617}\text{S}_{618}.$$

4. The peptide according to claim 1, wherein the peptide consists of (SEQ ID NO: 2)
$$\text{RILAVERYLKDQQLLGIWG}\overset{\frown}{\text{C}_{603}\text{SGKLIC}_{609}}\text{TTAVPF}_{615}\textbf{N}.$$

5. The peptide according to claim 1, wherein the peptide consists of (SEQ ID NO: 3)
$$\text{RILAVERYLKDQQLLGIWG}\overset{\frown}{\text{C}_{603}\text{SGKLIC}_{609}}\text{TTAVPG}_{615}\textbf{N}.$$

6. The peptide according to claim 1, wherein the peptide consists of (SEQ ID NO: 4)
$$\text{RILAVERYLKDQQLLGIWG}\overset{\frown}{\text{C}_{603}\text{SGKLIC}_{609}}\text{TTAVPG}_{615}\textbf{NA}_{617}\textbf{S}_{618}.$$

7. An antigenic composition comprising a peptide according to claim 3 in combination with a carrier or diluent.

8. An antigenic composition comprising a peptide according to claim 4 in combination with a carrier or diluent.

9. An antigenic composition comprising apeptide according to claim 5 in combination with a carrier or diluent.

10. An antigenic composition comprising a peptide according to claim 6 in combination with a carrier or diluent.

11. A process for preparation of the cyclic peptide of claim 1 comprising the steps of:
   a) reacting resin 9-fluorenylmethyloxycarbonyl (Fmoc) with reagents 2-(1H-b enzotriazol-1-yl)-1,1,3,3-tetramethyluronium tetrafluoroborate (TBTU) and N-hydroxybenzotriazole (HOBt), in a ratio (moles/moles) reagents/substitutable groups on the resin equal to 5, to effect a resin-bound linear peptide;
   b) contacting the resin-bound linear peptide with a trifluoroacetic acid solution, to separate the linear peptide from the resin;
   c) contacting the linear peptide in solution with an ether solution, to precipitate the linear peptide;
   d) purifying the precipitated linear peptide by high performance liquid chromatography (HPLC); and
   e) oxidizing the purified linear peptide to effect the cyclic peptide.

12. A method for in vitro detection of anti-HIV-1 antibodies in a biological sample comprising the steps of:
   a) bringing the biological sample into contact with at least one peptide of HIV-1 virus gp41 of sequence (III) as defined in claim 1;
   b) incubating the sample-and-peptide mixture under conditions permitting the formation of antigen-antibody complexes between the at least one peptide of sequence (III) and anti-HIV-1 antibodies present in the biological sample;
   c) washing the mixture; and
   d) revealing and detecting the antigen-antibody complexes formed.

13. A method for the in vitro detection of anti-HIV-1 antibodies and anti-HIV-2 antibodies in a biological sample comprising the steps of:
   a) bringing the biological sample into contact with (i) at least one peptide of gp41 of sequence (III) as defined in claim 1 and (ii) an HIV-2 antigen;
   b) incubating the sample-peptide-antigen mixture under conditions permitting the formation of antigen-antibody complexes (i) between the at least one peptide of sequence (III) and anti-HIV-1 antibodies present in the biological sample and (ii) between the HIV-2 antigen and anti-HIV-2 antibodies present in the biological sample;
   c) washing the mixture; and
   d) revealing and detecting the antigen-antibody complexes formed.

14. A method for the in vitro detection of anti-HIV-1 antibodies and anti-HIV-1 O antibodies in a biological sample comprising the steps of:
   a) bringing the biological sample into contact with at least one peptide of gp41 of sequence (III) as defined in claim 1 and an HIV-1 O antigen:
   b) incubating the sample-peptide-antigen mixture under conditions permitting the formation of antigen-antibody complexes (i) between the at least one peptide of sequence (III) and anti-HIV-1 antibodies present in the biological sample and (ii) between the HIV-1 O antigen and anti-HIV-1 O antibodies present in the biological sample;
   c) washing said mixture; and
   d) revealing and detecting the antigen-antibody complexes formed.

15. A method for the in vitro detection of anti-HIV-1 antibodies anti-HIV-1 O antibodies, and of anti-HIV-2 antibodies in a biological sample comprising the steps of:
   a) bringing the biological sample into contact with a first HIV-1 antigenic composition consisting of at least one peptide of gp41 of sequence (III), as defined in claim 1, a second antigen consisting of an HIV-1 O antigen, and a third antigen consisting of an HIV-2 antigen;
   b) incubating the mixture under conditions permitting the formation of antigen-antibody complexes between the peptide(s) of sequence (III) and anti-HIV-1 antibodies present in the biological sample, between the HIV-1 O antigen and anti-HIV-1 O antibodies present in the biological sample, and between the HIV-2 antigen and anti-HIV-2 antibodies present in the biological sample;
   c) washing the mixture; and
   d) revealing and detecting the antigen-antibody complexes formed.

16. A method for the in vitro detection of anti-HIV-1 antibodies in a biological sample comprising the steps of:
   a) bringing the biological sample into contact with a composition according to claim 2;
   b) incubating the sample-and-composition mixture under conditions permitting the formation of antigen-antibody complexes between the at least one peptide of sequence (III) and anti-HIV-1 antibodies present in the biological sample;
   c) washing the mixture; and
   d) revealing and detecting the antigen-antibody complexes formed.

* * * * *

SEQUENCE LISTING

```
<160> NUMBER OF SEQ ID NOS: 15

<210> SEQ ID NO 1
<211> LENGTH: 35
<212> TYPE: PRT
<213> ORGANISM: Human immunodeficiency virus type 1
<220> FEATURE:
<221> NAME/KEY: DISULFID
<222> LOCATION: (20)..(26)

<400> SEQUENCE: 1

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Phe
            20                  25                  30

Asn Ala Ser
        35

<210> SEQ ID NO 2
<211> LENGTH: 33
<212> TYPE: PRT
<213> ORGANISM: Human immunodeficiency virus type 1
<220> FEATURE:
<221> NAME/KEY: DISULFID
<222> LOCATION: (20)..(26)

<400> SEQUENCE: 2

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Phe
            20                  25                  30

Asn

<210> SEQ ID NO 3
<211> LENGTH: 33
<212> TYPE: PRT
<213> ORGANISM: Human immunodeficiency virus type 1
<220> FEATURE:
<221> NAME/KEY: DISULFID
<222> LOCATION: (20)..(26)

<400> SEQUENCE: 3

Arg Ile Leu Ala Val Glu Arg Tyr Leu Lys Asp Gln Gln Leu Leu Gly
```

```
                1               5                  10                  15
Ile Trp Gly Cys Ser Gly Lys Leu Ile Cys Thr Thr Ala Val Pro Gly
                20                  25                  30

Asn

<210> SEQ ID NO 4
<211> LENGTH: 35
<212> TYPE: PRT
<213> ORGANISM: Human immunodeficiency virus type 1
<220> FEATURE:
<221> NAME/KEY: DISULFID
<222> LOCATION: (20)..(26)

<400> SEQUENCE: 4

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Gly
                20                  25                  30

Asn Ala Ser
        35

<210> SEQ ID NO 5
<211> LENGTH: 35
<212> TYPE: PRT
<213> ORGANISM: Human immunodeficiency virus type 1
<220> FEATURE:
<221> NAME/KEY: DISULFID
<222> LOCATION: (20)..(26)
<220> FEATURE:
<221> NAME/KEY: MISC_FEATURE
<222> LOCATION: (32)..(32)
<223> OTHER INFORMATION: Xaa = Phe or Gly
<220> FEATURE:
<221> NAME/KEY: MISC_FEATURE
<222> LOCATION: (34)..(35)
<223> OTHER INFORMATION: Xaa Xaa = absent or Ala Ser

<400> SEQUENCE: 5

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Xaa
                20                  25                  30

Asn Xaa Xaa
        35

<210> SEQ ID NO 6
<211> LENGTH: 35
<212> TYPE: PRT
<213> ORGANISM: Human immunodeficiency virus type 1
<220> FEATURE:
<221> NAME/KEY: MISC_FEATURE
<222> LOCATION: (32)..(32)
<223> OTHER INFORMATION: Xaa = Phe or Gly
<220> FEATURE:
<221> NAME/KEY: MISC_FEATURE
<222> LOCATION: (34)..(35)
<223> OTHER INFORMATION: Xaa Xaa = absent or Ala Ser

<400> SEQUENCE: 6

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Xaa
                20                  25                  30

Asn Xaa Xaa
        35
```

```
<210> SEQ ID NO 7
<211> LENGTH: 35
<212> TYPE: PRT
<213> ORGANISM: Human immunodeficiency virus type 1
<220> FEATURE:
<221> NAME/KEY: DISULFID
<222> LOCATION: (20)..(26)

<400> SEQUENCE: 7

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Trp
            20                  25                  30

Asn Ala Ser
        35

<210> SEQ ID NO 8
<211> LENGTH: 21
<212> TYPE: PRT
<213> ORGANISM: Human immunodeficiency virus type 1

<400> SEQUENCE: 8

Arg Ile Leu Ala Val Glu Arg Tyr Leu Lys Asp Gln Gln Leu Leu Gly
1               5                   10                  15

Ile Trp Gly Cys Ser
            20

<210> SEQ ID NO 9
<211> LENGTH: 26
<212> TYPE: PRT
<213> ORGANISM: Human immunodeficiency virus type 1

<400> SEQUENCE: 9

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys
            20                  25

<210> SEQ ID NO 10
<211> LENGTH: 35
<212> TYPE: PRT
<213> ORGANISM: Human immunodeficiency virus type 1

<400> SEQUENCE: 10

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Trp
            20                  25                  30

Asn Ala Ser
        35

<210> SEQ ID NO 11
<211> LENGTH: 7
<212> TYPE: PRT
<213> ORGANISM: Human immunodeficiency virus type 1

<400> SEQUENCE: 11

Cys Ser Gly Lys Leu Ile Cys
1               5

<210> SEQ ID NO 12
<211> LENGTH: 9
<212> TYPE: PRT
```

```
<213> ORGANISM: Human immunodeficiency virus type 1

<400> SEQUENCE: 12

Trp Gly Cys Ser Gly Lys Leu Ile Cys
1               5

<210> SEQ ID NO 13
<211> LENGTH: 9
<212> TYPE: PRT
<213> ORGANISM: Human immunodeficiency virus type 1

<400> SEQUENCE: 13

Trp Gly Cys Ala Phe Arg Gln Val Cys
1               5

<210> SEQ ID NO 14
<211> LENGTH: 9
<212> TYPE: PRT
<213> ORGANISM: Human immunodeficiency virus type 1

<400> SEQUENCE: 14

Trp Gly Cys Lys Gly Lys Leu Ile Cys
1               5

<210> SEQ ID NO 15
<211> LENGTH: 9
<212> TYPE: PRT
<213> ORGANISM: Human immunodeficiency virus type 1

<400> SEQUENCE: 15

Trp Gly Cys Lys Gly Lys Leu Val Cys
1               5
```